United States Patent
Fillery

(10) Patent No.: US 7,645,420 B2
(45) Date of Patent: Jan. 12, 2010

(54) METHOD FOR SANITATION OF DENTAL WATER LINES

(76) Inventor: Edward David Fillery, 500 Queens Quay West, Suite 105E, Toronto, ON (CA) M5V 3K8

( * ) Notice: Subject to any disclaimer, the term of this patent is extended or adjusted under 35 U.S.C. 154(b) by 0 days.

(21) Appl. No.: 12/153,153

(22) Filed: May 14, 2008

(65) Prior Publication Data

US 2008/0299004 A1 Dec. 4, 2008

Related U.S. Application Data

(63) Continuation of application No. 11/209,607, filed on Aug. 24, 2005, now abandoned.

(51) Int. Cl.
*A61L 2/18* (2006.01)

(52) U.S. Cl. .................. 422/28; 137/15.04; 137/15.05; 210/764; 433/80

(58) Field of Classification Search .................. 422/28, 422/105, 292; 210/764; 433/80, 98; 137/15.01, 137/15.04, 15.05; 134/22.12
See application file for complete search history.

(56) References Cited

U.S. PATENT DOCUMENTS

| | | | | |
|---|---|---|---|---|
| 3,524,676 A | * | 8/1970 | Cocherell et al. | 297/188.21 |
| 5,044,952 A | * | 9/1991 | Castellini | 433/84 |
| 6,482,370 B2 | * | 11/2002 | Holsclaw et al. | 422/186.12 |
| 6,991,458 B2 | | 1/2006 | Castellini | |
| 2005/0199535 A1 | * | 9/2005 | Yates | 210/104 |

* cited by examiner

*Primary Examiner*—Sean E Conley
(74) *Attorney, Agent, or Firm*—I. Schmidt

(57) ABSTRACT

An automated flushing system removes stagnant water and the micro-organisms it contains from dental unit waterlines when a dental chair is not in use. The system prevents the exponential replication of micro-organisms in dental waterlines and can be used to increase the contact time of disinfectants with adherent biofilms in waterlines.

9 Claims, 1 Drawing Sheet

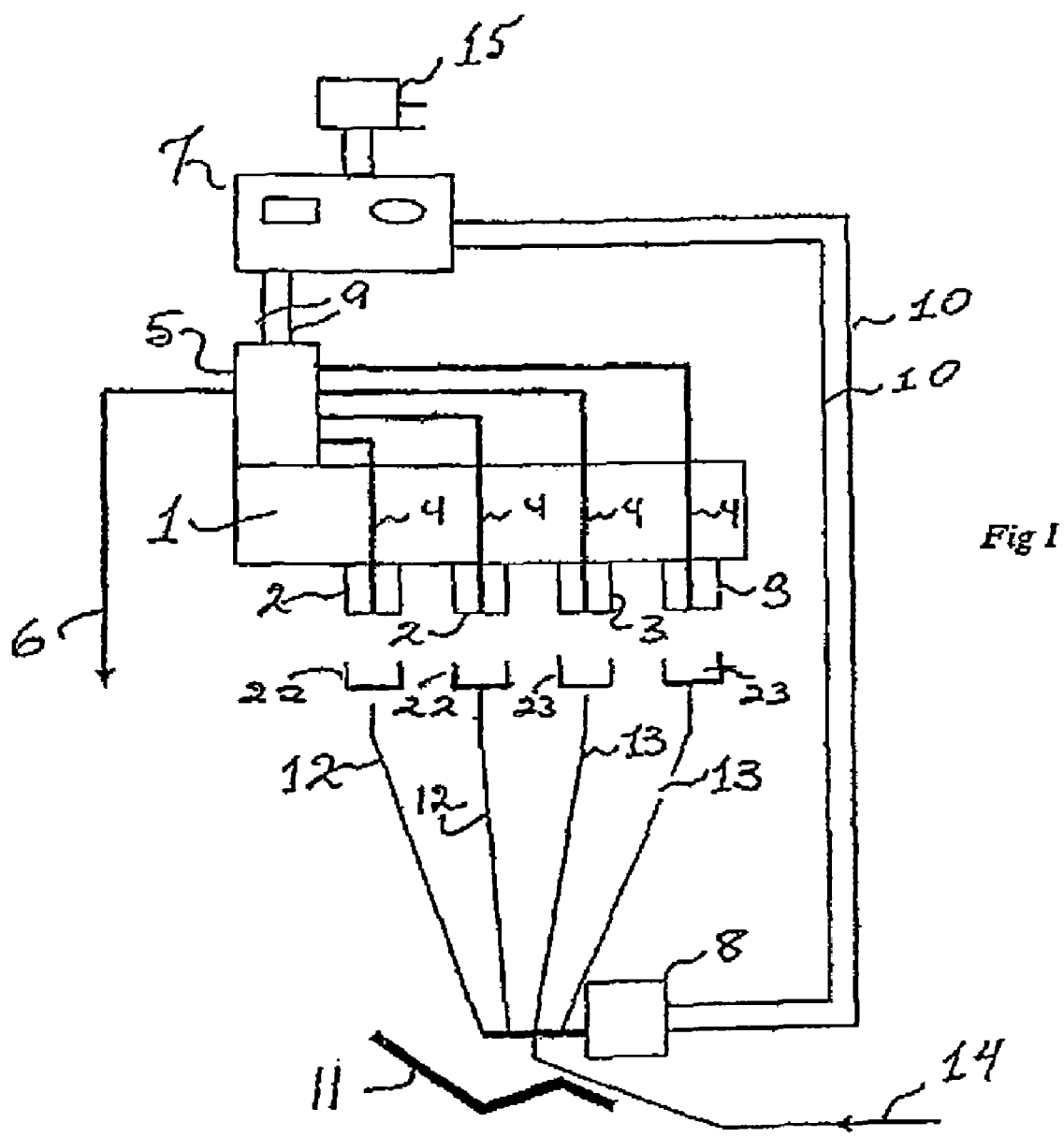
Fig I

METHOD FOR SANITATION OF DENTAL WATER LINES

RELATED APPLICATION

This application is a continuation of U.S. patent application Ser. No. 11/209,607 filed Aug. 24, 2005, the contents of which are hereby incorporated herein by reference

TECHNICAL FIELD

This invention relates to sanitation in dental unit waterlines in order to prevent the accumulation in the waterlines of hazardous biofilm.

BACKGROUND INFORMATION

Since the installation in dental handpieces and dental air/water syringes of anti-retraction valves to prevent back-contamination by patients' saliva, the main source of microbial contamination of dental waterlines is in the source water. Most jurisdictions provide mains tap water with less than the American Dental Association guideline of 200 CFUs/mL, but the low flow rates of water used in most dental procedures and the small bores of dental unit waterlines allow the build up of biofilm in dental waterlines. Thus counts of 10,000-100,000 CFU/mL are not uncommon in water leaving the cooling water nozzle of high-speed dental drills and from dental air/water syringes. Even when sterile water is delivered to bottled-water-fed dental units, it is not unusual for stray contaminating bacteria to enter the waterlines and multiply exponentially with the result of CFU counts the same as in tap-water-fed dental units. In some circumstances, bacteria are able to replicate every 20 minutes, which means one bacterium left in a waterline after the last treatment at, for instance 5:00 pm could have multiplied to over 2 million by midnight.

Even though the potential flow-rate of water through most dental unit waterlines to the high-speed drill is in the order of 60 mL per minute, most drilling operations require flow-rates much below this for adequate cooling and only a small portion of each patient's treatment actually involves drilling. Thus, ample opportunity occurs for bacterial accumulation even during office hours and very little actual flushing occurs. This means that even if water treatment devices such as the ozonizer described in U.S. Pat. No. 5,942,125 are installed, the contact time between ozone and the harmful biofilm is limited and restricted to office hours. Ozone in water decays to oxygen within 20-30 minutes and so any bacteria surviving the brief contact time and ozone decay have ample time to replicate.

The system described in U.S. Pat. No. 6,482,370 attempts to address this problem by installing a tee piece at the end of the waterline closest to the dental instrument (such as high-speed drill or air/water syringe) attached to a return tube that recirculates ozonized water back to the ozonizer. Unfortunately, such a tee piece and return tube constitute a considerable modification to hardware and plumbing of existing dental chairs and waterlines. In addition, during recirculation of the ozonized water, the ozonized water is not fed through the delivery structure for the dental instrument and any residual bacteria have the opportunity to multiply and contaminate the delivery structure so that when a freshly sterilized dental instrument is coupled to the dental water line, it too becomes contaminated. Meanwhile, while the recirculating ozonized water may kill bacteria, their toxic remains such as lipopolysaccharide (lps) are not purged from the system until a dental instrument is connected.

The present invention has been developed to alleviate these drawbacks.

SUMMARY OF THE INVENTION

Most dental unit waterlines contain water that is stagnant when the dental chair is not in use. The stagnant water allows micro-organisms contained in it to replicate exponentially during the times the dental chair is not in use. In accordance with this invention, water in waterlines and any micro-organisms that the water contains is flushed automatically for user-determined periods at user-determined intervals into a drain and disposed in a sewer.

In one embodiment of the invention, there is provided a manifold to which waterlines can be attached when the dental chair is not in use after high-speed drill handpiece(s) and air/water syringe handpieces have been disconnected (typically for sterilization). The manifold contains an electrically operated solenoid valve which, when electrically opened, flushes the waterlines to a drain. The solenoid valve is controlled by a programmable timer such as is known to those familiar with the art and typically used to control garden watering systems or to control household lamps while the homeowner is away.

The invention provides means to typically flush 1 litre of water from the dental unit waterlines over a five-minute period every hour that the dental chair is not in use at night and over weekends. The invention flushes out any accumulated micro-organisms, and increases the contact time of any adherent biofilm to fresh water containing chlorine, ozone or any other disinfectant, as desired. The invention requires little if any modification of waterlines or plumbing in existing dental chairs.

BRIEF DESCRIPTION OF THE DRAWINGS

In order to better understand the invention, an exemplary embodiment is described below with reference to the accompanying drawing, in which:

FIG. 1 is a schematic layout showing a manifold, solenoid and timer incorporated into a dental unit water line system in accordance with the invention.

DETAILED DESCRIPTION OF THE PREFERRED EMBODIMENT

Referring to the schematic in FIG. 1, the invention comprises a manifold (1) that contains one or more (typically 2) male connectors (2) onto which can be screwed female connectors 22 typically found on the ends of existing dental unit waterlines (12) and which would normally be connected to high-speed dental drill handpieces (not shown). The manifold also contains one or more (typically 2) male connectors (3) to which can be screwed female connectors 23 typically found on the ends of existing dental unit waterlines (13) and which would normally be connected to air/water syringe handpieces (not shown). Tubes (4) carry water from the connectors (2, 3) to an electrically operated solenoid valve (5) attached to the manifold (1), which when open, flushes water to a drain connector (6). The electrically operated solenoid valve (5) is connected by wires (9) to a programmable timer switch (7) which automatically controls the opening of the valve. The programmable timer switch (7) is also connected by wires (10) to a solenoid valve (8) which overrides an air-operated valve typically used in an existing dental chair (11) to enable cooling water to flow to the high-speed drill handpiece. Valve (8) is necessary because cooling water is normally only fed to the high-speed drill when air (controlled by a foot pedal or other switch) is operating the turbine motor of the dental drill. Automatic actuation of the solenoid valve (5) also actuates the valve (8) so that water will flow through the dental water lines (12) for high-speed dental drill handpieces as well as the water lines (13) for air/water syringe handpieces.

Water flows to the typical dental unit waterlines in existing dental chairs from a water supply (14) which could be the mains water supply, a water ozonizer, or a bottled water system. The programmable timer switch (7) would typically be powered by 24 volts ac from a transformer (15) connected to a mains electricity supply. The program, previously entered to suit the schedule and cleaning needs of the dental office, is retained in the memory of the programmable timer switch (7) by a battery supply when not plugged into the mains electricity.

Whenever a dental chair (11) is not being used, such as at night, at weekends or during lunch breaks, the dentist or assistant disconnects the dental drill handpiece which is then cleaned and sterilized in preparation for the next patient in accordance with recommended practice. Air/water syringe handpieces are also typically removed for cleaning and sterilization. Rather than place the tubing and connectors (22, 23) in their normal resting place in slots on the dental chair table, the waterlines (12,13) are connected to the connectors (2, 3) on the manifold (1) as depicted in FIG. 1. At set time points, the switch (7) directs power (typically 24 volts ac) to the solenoid valve (5) which opens and flushes water from the dental unit water lines, removing harmful micro-organisms. After a set time period, the programmable timer (7) switches off power to the electrically operated solenoid (5) and the flushing ends.

To resume normal operation of the dental chair, the water lines (12, 13) are disconnected from the manifold (1) and coupled to the high-speed drill handpieces and air/water syringes, as required.

Variations may be made to the above-described embodiment of the invention as will be apparent to those skilled in the art. In particular, the invention provides for the solenoid valve (5) to be automatically actuated by an actuator which is adapted to detect the presence of biofilm in the dental water lines. Upon detection of biofilm exceeding a pre-determined level, the solenoid valve (5) may operate to allow water to flow through the dental water lines until a reduced biofilm is detected or for a predetermined time interval.

The invention claimed is:

1. Method for sanitizing dental water lines in a dental chair having dental water lines coupled to a water supply at one end and dental water line connectors on ends of said dental water lines remote from said water supply, in which the method includes the following sequential steps:

removing all dental instruments which are coupled to said dental water line connectors, coupling the dental water line connectors directly to a manifold, said manifold operatively connected to the water supply to flow water through said dental water lines, said dental water line connectors, said manifold, a solenoid valve, and a drain, automatically and periodically flushing water from the water supply directly through the dental water lines, the dental water line connectors, the manifold, the solenoid valve, and to the drain, for predetermined intervals to directly discharge biofilm contaminated water from the manifold directly through the solenoid valve and from the solenoid valve directly to the drain.

2. Method according to claim 1 in which 1 liter of water is flushed to drain for a five minute period every hour.

3. Method according to claim 1 in which water is flushed to drain during periods of time when a dental chair is typically not in use.

4. Method according to claim 1 in which automatic flushing to dram of water occurs when the presence of bioflim in the water supply through the dental water lines exceeds a pre-determined level.

5. Method according to claim 1 in which the water supply contains disinfectant.

6. Method according to claim 5 in which the water supply is disinfected with ozone.

7. Method according to claim 1 including allowing water to flow through dental water line connectors for high-speed dental drill handpieces so as to override any air-actuated switches for high-speed dental drill handpieces.

8. Method for sanitizing dental water lines in a dental chair having dental water lines coupled to a water supply at one end and dental water line connectors on ends of said dental water lines remote from said water supply, in which the method includes the following sequential steps:

removing all dental instruments which are coupled to said dental water line connectors, providing a manifold for coupling to the dental water line connectors, providing a solenoid actuated first valve for allowing water from the water supply to flow through said dental water lines, dental water line connectors, the manifold, and to a drain, providing an actuator for automatically actuating the solenoid actuated first valve for predetermined intervals and periodically flushing water from the water supply through the dental water lines, the dental water line connectors, the manifold, the solenoid valve, and to the drain to discharge biofilm contaminated water from the manifold directly though the solenoid valve, and from the solenoid valve directly to the drain.

9. Method according to claim 8 in which the method includes providing a second valve coupled to the actuator, the second valve being adapted to allow water to flow through dental water line connectors for high-speed dental drill handpieces so as to override any air-actuated switches for high-speed dental drill handpieces whenever the solenoid actuated first valve is actuated to allow water to flow through the dental water lines, the dental water line connectors and the manifold directly to drain.

* * * * *